United States Patent [19]

Castelijns et al.

[11] Patent Number: 4,649,211

[45] Date of Patent: Mar. 10, 1987

[54] PROCESS FOR THE PREPARATION OF 2-CYANOMETHYLCYCLOHEXANONE

[75] Inventors: Anna M. C. F. Castelijns; Thomas M. G. Aarts, both of Stein (L.), Netherlands

[73] Assignee: Stamicarbon B.V., Geleen, Netherlands

[21] Appl. No.: 649,653

[22] Filed: Sep. 12, 1984

[30] Foreign Application Priority Data

Sep. 16, 1983 [NL] Netherlands .................. 8303206

[51] Int. Cl.[4] .................. C07C 120/00; C07C 121/46
[52] U.S. Cl. ..................................... 558/430; 558/351
[58] Field of Search .................. 260/464; 558/351, 430

[56] References Cited

FOREIGN PATENT DOCUMENTS 959092 2/1957 Fed. Rep. of Germany ...... 260/464

OTHER PUBLICATIONS

C.A. 56:339 (1962), Trave et al.
On the Synthesis of Cyclohexanone-(2)-Acetic Acid-(1) by Alfred Dornow & Ernst Fleischmann; Chemische Berichte, 88, (1955), pp. 1340-1345.
Chimica Organica—Sintesi di Cicloalchen-I-il-Etilamine by Roberto Trave and Giuseppe Bianchetti—Extract, p. 821, Translation Considered, Atti. Accad. Nazl. Lincei Rend., (1960), Classe Sci. Fis., Mat c Nat. 28, pp. 814-823.

*Primary Examiner*—Joseph Paul Brust
*Attorney, Agent, or Firm*—Cushman, Darby & Cushman

[57] ABSTRACT

The invention relates to a process for the preparation of 2-cyanomethylcyclohexanone by 1. converting cyclohexanone to a Mannich base with a secondary amine salt and formaldehyde
2. converting the Mannich base to the corresponding cyanohydrin with a cyanide
3. pyrolysing the cyanohydrin obtained in step 2, wherein the pyrolysis of the cyanohydrin is carried out in the presence of a polar, aprotic solvent having a boiling point of more than 140° C. and/or sodium cyanide.

8 Claims, No Drawings

PROCESS FOR THE PREPARATION OF 2-CYANOMETHYLCYCLOHEXANONE

The invention relates to a process for preparing 2-cyanomethylcyclohexanone by converting cyclohexanone to a Mannich base with a secondary amine salt and formaldehyde in a first step, then converting the Mannich base into the cyanohydrin with a cyanide in a second step, and finally pyrolysing the cyanohydrin so obtained in a third step.

Such a process is known from the German patent specification No. DE-C-959092. According to the first step of that process a Mannich base can be formed, in an aqueous medium, from cyclohexanone, formaldehyde and a secondary amine having the general formula HN—$R_1R_2$.HX, where $R_1$ and $R_2$ each represent an alkyl group and X the radical of a strong acid, the Mannich base having the general formula

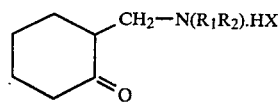

where $R_1$, $R_2$ and X have the above-described meanings. After addition of water the organic layer is separated off and the aqueous layer is extracted with ether to remove the cyclohexanone and is subsequently evaporated in vacuo. In the second step the Mannich base is reacted with 1½ moles of KCN per mole of secondary amine used to yield the cyanohydrin having the general formula

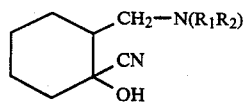

where $R_1$ and $R_2$ have the same meanings as described above. The cyanohydrin formed forms an organic layer which is dried after the aqeuous phase has been separated off. Finally, in the third step, the cyanohydrin is at 150° C. pyrolysed to 2-cyanomethylcyclohexanone. In the said German patent specification a yield of 75% is reported for the formation of the desired product. However, applicant has found that a significant portion of this yield is a dimer product of 2-methylenecyclohexanone having the formula

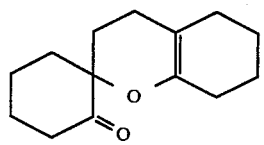

The object of the invention is a high-yield process for the preparation of 2-cyanomethylcyclohexanone. 2-Cyanomethylcyclohexanone can be used as a raw material for the preparation of indole. According to the present invention 2-cyanomethylcyclohexanone is prepared by 1. converting cyclohexanone to a Mannich base with a secondary amine salt and formaldehyde
2. converting the Mannich base to the corresponding cyanohydrin with a cyanide
3. pyrolysing the cyanohydrin obtained in step 2 wherein the pyrolysis of the cyanohydrin is carried out in the presence of a polar, aprotic solvent heaving a boiling point of more than 140° C. and/or sodium cyanide. With the process according to the invention it is found that dimer formation can be reduced.

The reduction of dimer formation can be achieved in a number of ways. In a first mode of realization the cyanohydrin-containing layer obtained in the second step is dissolved in the polar, aprotic solvent to obtain a solution containg 5–60 wt% cyanohydrin, and the cyanohydrin is pyrolysed by heating the solution so obtained at 100°–170° C. for 1–3 hours. In a second mode of realization a cyanide is added to the cyanohydrin-containing layer in an amount of 0.2–5 wt %, relative to the amount of cyanohydrin. The pyrolysis is then carried out in the same manner. It is also possible to use a polar, aprotic solvent as well as a cyanide in the pyrolysis. The first and the second step of the process according to the invention can be effected in various ways. Preferably, no extra water is added after the reaction in the first step, in which the Mannich base is formed. This is because applicant has found that the aqueous phase can be used as such in the second step. In this way, the process is simplified. Applicant has also found that in the second step only 1 mole of cyanide need be added per mole of secondary amine salt used in the first step. This makes the processing of the cyanide-containing waste-water stream less costly. Moreover, the organic layer containing the cyanohydrin can after draining of the aqueous layer be used in the third step without further crystallization and drying, which means a simplification of the process.

In the process according to the invention, as secondary amine salt a salt can be used which has, for example, the general formula HN—$R_1'R_2'$.Hx, $R_1'$ and $R_2'$ being identical or different and representing an alkyl group with 1–3 C-atoms or $R_1'R_2'$ representing a cyclic compound —$(CH_2)_n$— with n=4 or 5, and X representing the anion of a strong acid, for example a chloride or a bromide. Preferably, dimethylamine hydrochloride is used.

Examples of polar, aprotic solvents having a boiling point above 140° C. that can be used in the process according to the invention are dimethyl formamide (DMF), dimethyl sulphoxide (DMSO) and hexamethylphosphoric triamide (HMPTA). Preferably, cheap DMF is used.

The cyanide to be used in the second step is preferably KCN of NaCN.

The invention is further explained in the following examples.

EXAMPLE I

A mixture of 245.4 g of cyclohexanone (2.5 mol), 40.7 g of dimethylamine. HCl (0,5 mol) and 41.0 g of 37 wt % formaline (0.5 mol formaldehyde) was in 1½ hours heated to 70° C. while being stirred well. This temperature was maintained for 30 minutes, after which the mixture was cooled down in about 45 minutes. After addition of 150 ml of water the organic layer was separated off and the aqueous layer was extracted four times with 50 ml of ether. Next, the aqueous layer was subjected to an in vacuo evaporation treatment. After this treatment 110.8 g of moist product was obtained. The Mannich base so obtained was dissolved in 150 ml of water. To this solution of 36.8 g of NaCN (0.75 mol) in 100 ml of water was added. During this addition the temperature rose to 45° C., which temperature was maintained for 1 hour. After cooling, the cyanohydrin-containing top layer was separated off and the aqueous layer was three times extracted with 30 ml of ether. Next, the top layer and the ether extracts were mixed and evaporated. The yield was 87.5 g (96% relative to dimethylamine.HCl). The precipitate was subsequently dried overnight over $H_2SO_4$.

After this drying operation the weight of the cyanohydrin was 81.4 g. Next, 12.0 g of the 2-(dimethylaminomethyl)-cyclohexanone-cyanohydrin so obtained was dissolved in 50 ml of DMF and pyrolysed at 140° C. for 2 hours.

The evolving dimethylamine was caught in dilute hydrochloric acid. The residue was distilled. After distillation 7.2 g of product appeared to have been formed. From gas-liquid chromatographic (GLC) analysis it appeared that this product was pure 2-cyanomethylcyclohexanone, having a boiling point of 128° C. at 7.2 mbar. The efficiency of the pyrolysis was 80%, the overall efficiency 77%.

Comparative example I 2-(Dimethylaminomethyl)-cyclohexanone-cyanohydrin was prepared in the manner described in example I. Without addition of DMF, 25 g of it was pyrolysed at 140° C. for 2 hours. Distillation at 148° C. and 19.7 mbar yielded 14 g of product, which was analysed by GLC. It was found that a mixture had been formed which was difficult to separate, 80% of which was 2-cyanomethylcyclohexanone and 20% a dimer of 2-methylenecyclohexanone. It follows that the efficiency of the pyrolysis to desired product as 60%, the overall efficiency being 57%.

EXAMPLE II 2-(Dimethylaminomethyl)-cyclohexanone-cyanohydrin was prepared in the manner described in example I. To 15.1 g of 2-(dimethylaminomethyl)-cyclohexanone-cyanohydrin 0.7 g of NaCN (4.6 wt %, relative to cyanohydrin) was added, after which the cyanohydrin was pyrolysed at 140° C. for 2 hours. Distillation was done in the manner described in comparative example I. GLC analysis showed that a mixture had been formed with a ratio of desired product to dimer of 93:7. The overall efficiency was 65%.

EXAMPLE III

A mixture of 654 g of cyclohexanone (6.66 mol), 109.4 g of dimethylamine.HCl (1.33 mol) and 107.8 g of 37 wt % formaline (1.33 mol formaldehyde) was in 1½ hours heated to 70° C. while being stirred well, after which this temperature was maintained for half an hour. Next, the mixture was cooled to 20° C. and the organic, cyclohexanone-containing layer was separated off.

To the aqueous layer containing Mannich base, 200 ml of water was added in which 98.8 g of NaCN (2.02 mol) had been dissolved. During this addition, the temperature rose to 47° C. The mixture was kept at a temperature of 40° C. for 1 hour.

After cooling, the cyanohydrin-containing top layer was separated from the aqueous layer. The weight of the top layer was 272.5 g. Next, this layer was dissolved in 250 ml of DMF and pyrolysed at 112° C. for 1 hour. The temperature of the reaction mixture did not rise further during pyrolysis, on account of the water still present. After distillation, GLC analysis showed that pure 2-cyanomethylcyclohexanone had been formed. The overall efficiency was 75%.

What is claimed is:

1. A process for the preparation of 2-cyanomethylcyclohexanone which consists essentially of:

forming the strong acid salt of the Mannich base of cyclohexanone by reaction of cyclohexanone with formaldehyde and the strong acid salt of a secondary amine of the general formula $HNR_1R_2$ wherein $R_1$ and $R_2$ independently represent a $C_1$–$C_3$ alkyl group or together represent —$(CH_2)_n$— wherein n=4 or 5, converting said Mannich base acid salt directly to the corresponding cyanohydrin by reaction with sodium or potassium cyanide, dissolving the thus-obtained cyanohydrin in a polar, aprotic solvent having a boiling point of at least 140° C. to obtain a solution containing 5–60 wt % cyanohydrin, and pyrolysing the cyanohydrin, without additional water being added, at a temperature of from 100° C. to 170° C.

2. Process according to claim 1, wherein the Mannich base formed in the first step is separated off as aqueous solution and this solution is directly used in the second step.

3. Process according to claim 1, wherein in the second step the cyanide is used in an amount of 1 mole per mole of secondary amine salt used in the first step.

4. Process according to claim 1, wherein dimethylamine hydrochloride is used as secondary amine salt.

5. Process according to claim 1, wherein dimethyl formamide is used as the polar, aprotic solvent.

6. Process as claimed in claim 1, wherein said pyrolysis of cyanohydrin occurs at a temperature from 100° to 170° C. in the presence of sodium cyanide.

7. Process as claimed in claim 1, wherein said polar, aprotic solvent is a member of the group consisting of dimethyl formamide, dimethyl sulphoxide and hexamethylphosphoric triamide.

8. A process for the preparation of 2-cyanomethylcyclohexanone which consists essentially of;

forming the strong acid salt of the Mannich base of cyclohexanone by reaction of cyclohexanone with formaldehyde and the strong acid salt of a secondary amine of the general formula $HNR_1R_2$ wherein $R_1$ and $R_2$ independently represent a $C_1$–$C_3$ alkyl group or together represent —$(CH_2)_n$— wherein n=4 or 5, converting said Mannich base acid salt directly to the corresponding cyanohydrin by reaction with sodium cyanide, dissolving the thus-obtained cyanohydrin in a polar, aprotic solvent having a boiling point of at least 140° C. to obtain a solution containing 5–60 wt.% cyanohydrin, wherein said polar aprotic solvent is a member of the group consisting of dimethyl formamide, dimethyl sulphoxide and hexamethylphosphoric triamide, and pyrolysing the cyanohydrin, without additional water being added, at a temperature of from 100° to 170° C.

* * * * *